United States Patent

Syukuda et al.

[11] 4,455,297
[45] Jun. 19, 1984

[54] METHOD FOR PRODUCING PERTUSSIS TOXOID

[75] Inventors: Yukio Syukuda; Hideo Watanabe; Shigeo Matsuyama, all of Hikari, Japan

[73] Assignee: Takeda Chemical Industries, Ltd., Osaka, Japan

[21] Appl. No.: 408,563

[22] Filed: Aug. 16, 1982

Related U.S. Application Data

[63] Continuation of Ser. No. 229,931, Jan. 30, 1981, abandoned.

[30] Foreign Application Priority Data

Sep. 12, 1980 [JP] Japan ................................. 55-127825

[51] Int. Cl.³ ....................... A61K 39/10; C07G 7/00; C12P 21/00
[52] U.S. Cl. ......................................... 424/92; 424/88; 435/68; 260/112 R
[58] Field of Search .................... 424/88–92; 435/68; 260/112 R

[56] References Cited

U.S. PATENT DOCUMENTS

| | | | |
|---|---|---|---|
| 3,135,662 | 6/1964 | Pope et al. | 424/92 |
| 4,029,765 | 6/1977 | Helting et al. | 424/92 |
| 4,033,819 | 7/1977 | Helting et al. | 424/92 |
| 4,075,321 | 2/1978 | Relyveld | 424/92 |
| 4,242,270 | 12/1980 | Ayme et al. | 424/92 |

*Primary Examiner*—Blondel Hazel
*Attorney, Agent, or Firm*—Wegner & Bretschneider

[57] ABSTRACT

A pertussis toxoid is produced by removing endotoxin from a culture supernatant of a *Bordetella pertussis* phase I strain or a concentrate thereof and flocculating pertussis exotoxin in the resultant fluid by permitting formaldehyde to act upon the fluid in the substantial absence of basic amino acid. The thus-obtained pertussis toxoid is low in toxicity and has a high immunizing potency.

8 Claims, No Drawings

METHOD FOR PRODUCING PERTUSSIS TOXOID

This application is a continuation of application Ser. No. 229,931 filed Jan. 30, 1981, now abandoned.

This invention relates to a method of producing a pertussis toxoid.

Whooping cough is an infectious disease caused by *Bordetella pertussis* and produces serious effects especially in infants.

Vaccines have heretofore been employed for the prevention of this disease. However, because such vaccines are conventionally prepared from the whole cells of the causative bacterium, they give rise to fever and other serious side effects. It has therefore been an urgent social need to overcome these disadvantages.

Many attempts have been made in which an effective component only is isolated from *Bordetella pertussis* phase I strain and made into a vaccine, but none of the proposed procedures has been found to be satisfactory. Meanwhile, the proposition that the infection by *Bordetella pertussis* lies in the exotoxin released from the said bacteria (M. Pittmann: "Reviews of Infectious Diseases", 1, p. 401–412, 1979) suggested the possibility of protection by means of a pertussis toxoid but there has been no report indicating the success of obtaining a pertussis toxoid.

Against the above technical background, the present inventors have for the first time succeeded in producing a pertussis toxoid by a new method of detoxification.

Thus, the object of this invention is to provide a method of producing a pertussis toxoid which is low in toxicity and yet has a very high immunizing potency.

The said object can be realized by removing endotoxin from a culture supernatant or a concentrate thereof and flocculating pertussis exotoxin in the resultant fluid by permitting formaldehyde to act upon the fluid in the substantial absence of basic amino acid.

In accordance with this invention, there is employed a culture supernatant of a *Bordetella pertussis* phase I strain or a concentrate thereof. The cultivation of the *Bordetella pertussis* phase I strain can be carried out in a manner known per se. Thus, for example, the strain is cultivated in a liquid medium (Cohen-Wheeler medium, Stainer & Scholte medium, etc.) at about 35° to 37° C. for about 5 to 7 days. The supernatant of the resulting culture is collected by filtration or centrifugation. Either this supernatant fluid or a concentrate thereof can be used in the subsequent step of removing its endotoxin. The concentrate can be obtained by salting out which is conventional per se. Thus, for example, 2 to 5 kg of ammonium sulfate is added to 10 l each of the culture supernatant and, after mixing, the precipitate formed is collected by an expedient technique such as filtration or centrifugation. This precipitate is then dissolved in a suitable amount of 0.05 M phosphate buffer supplemented with 1 M sodium chloride, and the supernatant is obtained by centrifugal sedimentation or the like procedure to give a concentrated fluid.

In accordance with this invention, the above-mentioned supernatant or concentrate is treated to remove its endotoxin. This removal of the endotoxin can be accomplished by any of such procedures as sucrose density gradient centrifugation, potassium tartrate density gradient centrifugation, cesium chloride density gradient centrifugation, gel filtration, etc. A particularly advantageous procedure comprises centrifuging the above-mentioned supernatant or concentrate on a sucrose density gradient of about 0 to 60 W/W % at R max. about 62,000 to 122,000 G for about 10 to 24 hours.

The most essential feature of this invention is the step of flocculating pertussis exotoxin in the above obtained pertussis exotoxin fluid by permitting formaldehyde to act upon the fluid in the substantial absence of basic amino acid, whereby the exotoxin is substantially detoxified to yield pertussis toxoid. Thus, the precipitated-purified vaccine containing the thus-detoxified toxoid and the precipitated-purified pertussis-diphtheria-tetanus trivalent vaccine containing the same detoxified toxoid are low in toxicity and yet have very high immunizing potencies. Such effects cannot be achieved with the pertussis toxoid fluid prepared by permitting formaldehyde to act upon the pertussis exotoxin fluid in the substantial presence of basic amino acid, especially L-lysine.

Generally, the conventional bacterial exotoxins such as diphtheria toxin give only loose bindings between formaldehyde and toxin molecules and it was impossible to obtain a stable polymerizate without the aid of an additive substance such as a basic amino acid e.g. L-lysine. As regards pertussis exotoxin, however, it has been found unexpectedly that the formalin detoxification in the absence of such amino acid promotes on the contrary the polymerization of the exotoxin to give a flocculent antigen mass. This promotes the increase of immunity-competent molecule size, potentiates the immunogenecity and, hence, enables the production of a high-potency pertussis toxoid.

The above flocculating treatment is carried out by adding formalin (i.e. 37 W/V % aqueous solution of formaldehyde) or a dilution thereof with water to the pertussis exotoxin fluid in the substantial absence (i.e. less than 10 mM) of basic amino acid such as L-lysine and incubating the mixture until the pertussis exotoxin is substantially detoxified. It is usually advantageous to admix formalin or its dilution with the exotoxin fluid, with no addition of basic amino acid at all, to give a concentration of about 0.1 to 0.6 V/V % in terms of formalin and incubate the mixture, with or without further addition of formalin or its dilution up to a total concentration within the above range, at about 32° to 42° C. for about 3 to 14 days.

By the above treatment, the pertussis exotoxin is flocculated and thereby detoxified to yield a flocculent pertussis toxoid mass-containing suspension. The resultant flocculent toxoid mass in the suspension is dispersed by a suitable technique such as ultrasonication at about 10 to 50 kc to give a toxoid fluid.

In the method of this invention, a dialysis treatment may be interposed between the respective steps. Such dialysis can be carried out in a per se conventional manner.

Exactly in the same manner as the whole cell whooping cough vaccine fluid, the pertussis toxoid fluid thus obtained can be processed into a precipitated-purified pertussis vaccine or a precipitated-purified pertussis-diphtheria-tetanus trivalent vaccine and can be administered to humans.

The following Examples are further illustrative but not limitative of this invention.

The properties of Tohama phase I strain of *Bordetella pertussis* employed in the following Examples are disclosed in e.g. "Infection and Immunity", 6, p. 899–904 (1972). This strain has been maintained at National Institute of Health, Tokyo, Japan (NIHJ), and deposited at also Institute for Fermentation, Osaka, Japan under the accession number of IFO-14073.

Throughout the present specification as well as in claims, the abbreviations "μg", "mg", "g", "kg", "ml", "l", "°C.", "mM", "M", "r.p.m.", "kc", "R max." "G" "IU" and "Lf" respectively refer to "microgram(s),", "milligram(s)", "gram(s)", "kilogram(s)", "milliliter(s)", "liter(s)", "degree(s) centigrade", "millimolar concentration", "molar concentration", "revolution(s) per minute", "kilocycle(s)", "Radius maximum", "gravity", "international unit(s)" and "Limit of flocculation".

EXAMPLE 1

Tohama phase I strain of Bordetella pertussis was inoculated in a Bordet-Gengou medium prepared from potato, peptone, sodium chloride, agar and bovine blood and incubated at 35° C. for 2 days. Then, the translucent circular colonies were picked up and a colony reactive to the K agglutinating antibody was developed again on a Bordet-Gengou medium for use as a seed culture. A production medium was prepared by autoclaving a Cohen-Wheeler liquid medium (Table 1, hereafter) at 121° C. for 60 minutes and cooling it immediately to about 40° C. This medium was preserved at 37° C.

The seed culture prepared above was added to this production medium to give a terminal population of 200 to 300 million cells/ml, stirred well, inoculated into Roux bottles at the dose of 0.2 l per bottle and immediately cultivated in an incubator at 37° C. The incubation period depended on the cell growth conditions. The maximum cell yield was attained at the fifth day when the hemagglutinating (HA) titer of the culture fluid against chick erythrocytes (as determined by the method described in "Infection and Immunity", 7, p. 922–999 (1978) throughout the present specification) was also at a peak level. Therefore, the fluids were pooled and centrifuged, and 20.2 W/V % of ammonium sulfate was added to the supernatant. After stirring well, the mixture was allowed to stand at 4° C. After 7 days, the supernatant was siphoned off and the sediment was collected and centrifuged at 8,000 r.p.m. for 10 minutes. The supernatant was discarded. To the sediment was added 1/10 of the volume of the fluid pool of 1 M sodium chloride—0.05 M phosphate buffer (pH 8.0), and the mixture was stirred well. The mixture was allowed to stand again at 4° C. for 7 days, after which it was centrifuged again and the supernatant was collected (Extract I). This supernatant was rich in fimbriae, leukycytosis promoting factor (hereafter LPF), histamine sensitizing factor (hereafter HSF) and endotoxin but free from cells. Extract I was reconcentrated, an equal volume of saturated ammonium sulfate (adjusted to pH 8.0 with ammonia) was added thereto and the mixture was allowed to stand at 4° C. for 7 days. This ammonium sulfate fraction was centrifuged at 10,000 r.p.m. for 20 minutes to harvest the sediment and 1/300 of the volume of the fluid pool of 1 M sodium chloride—0.05 M phosphate buffer (pH 8.0) was added thereto. After thorough mixing, the mixture was put in a dialysis tube of semipermeable membrane to remove the ammonium sulfate, using a 1 M solution of sodium chloride (pH 8.0) as the external fluid. The dialyzed concentrate was then subjected to the following sucrose density gradient centrifugation.

A previously sterilized centrifugal rotor (capacity 1700 ml) and seal assembly was driven at a low speed and 1300 ml of 5 W/V % to 30 W/V % sucrose solutions were fed by means of a gradient pump. Then, 100 ml of the above dialyzed concentrate was fed and 300 ml of an overlay fluid (0.5 M sodium chloride solution, pH 8.0) was introduced. The rotor was driven at R max. 89,400 G for 18.5 hours.

After centrifugation, 34 W/V % sucrose solution was introduced at a low speed and the fluid within the rotor was collected in 50 to 100 ml fractions (collection of fractions). This collection was commenced from the low sucrose density side and the high HA-reactive (not less than 20 titers per ml, preferably not less than 500 titers per ml) and endotoxin-lean fractions were harvested. The scarcity of endotoxin was judged by a rabbit pyrogenicity test. Thus, each fraction sample was heated at 100° C. for 3 minutes and diluted to 20 HA titers/ml with physiological saline. This dilution was intravenously administered to rabbits at the dose of 1 ml per kg body weight. The fractions which did not cause fever within 3 hours were selected and pooled as the exotoxin fluid.

The exotoxin fluid was diluted with M/250 phosphate buffered saline (pH 7.0) to a proteinaceous N content of about 50 μg/ml. In this step, gelatin, Tween 80 (polyoxyethylene sorbitan monooleate; Kao-Atlas, Japan) and thimerosal were added to give the concentrations of 0.02 W/V % of gelatin, 0.05 V/V % of Tween 80 and 0.01 W/V % of thimerosal. To this fluid, without the addition of any basic amino acid, was added formalin to a concentration of 0.2 V/V % in an incubator at 39° C. and, after thorough mixing, was allowed to stand in the same incubator. After one day, an additional amount of formalin was added to a concentration of 0.3 V/V % and, after thorough mixing, the mixture was further incubated in the same incubator. After an additional 2 days, formalin was further added to a concentration of 0.4 V/V % and the mixture was stirred well and further incubated in the incubator for a total of 5 days. The resulting flocculated toxoic mass-containing suspension was dialyzed against 0.01 V/V % formalin-physiological saline as the external fluid. This dialysis was carried out by dialyzing the above suspension in a dialysis membrane tube against 12.5 times the volume of the internal fluid of said external fluid in a cold room (4° C.) for 2 days, with the external fluid being constantly agitated. The external fluid was replaced with a fresh one 2 days later and the dialysis was repeated. The dialyzed flocculent toxoid suspension was subjected to various tests applicable to pertussis stock vaccine and, then, used as a stock toxoid fluid. Before the preparation of a final bulk, the flocculent toxoid suspension was ultrasonicated (10 kc, 5 min.) and filtered through a 400 mesh strainer (Japanese Industrial Standard) to give a final pertussis toxoid fluid. As a control, the exotoxin fluid was treated with formalin with addition of 0.05 M L-lysine and subsequently treated as above to obtain a control fluid.

The pertussis toxoid fluid obtained as above and the control fluid were each treated according to the method of Levine (Reo Levine, Joseph L. Stone & Louise Wyman: Factors affecting the efficiency of the aluminum adjuvant in diphtheria and tetanus toxoid. J. Immunology 75, p. 301–307, 1955). Thus, each fluid was diluted with M/250 phosphate buffered saline (pH 7.0) to a protenaceous N content of 20 μg/ml or less, followed by addition of aluminum chloride to a concentration of 0.18 W/V %. The mixture was stirred well and adjusted to pH 7.0 with hydrochloric acid or sodium hydroxide to give an aluminum-precipitated vaccine of about 0.2 mg in terms of aluminum/ml. The properties of these products are shown in Table 2. After statistical processing, LPF is acceptable when it is not more than the equivalent of 0.5 LPU (Leukocytosis-promoting units as determined by the method described in "Medicine and Biology", 83, p. 117–123)/ml and not acceptable when otherwise. Similarly, HSF is acceptable when it is not more than the equivalent of 0.8 HSU (histamine sensitizing units as determined by the method described in "Journal of Biological Standardization", 7 (1979), p. 21–29)/ml and not acceptable when otherwise. The mouse protecting potency, similarly after statistical processing, is acceptable when it is at least 8 IU (challenged 3 weeks after the immunization)/ml or more and not acceptable when otherwise.

As is clear from Table 2, in accordance with the detoxification method of this invention, no rejects were found in regard to any of LPF, HSF and the mouse protecting potency throughout 14 consecutive production batches, the mean potency being 13.5 IU/ml. In contrast, when L-lysine had been added, a 23-batch series of production yielded 4 LPF rejects, 8 HSF rejects and 10 potency rejects, and the overall "acceptables" accounted only for 6/23=26%.

TABLE 1

| Soluble starch | 225 g |
|---|---|
| NaCl | 375 g |
| K H$_2$PO$_4$ | 75 g |
| MgCl$_2$.6H$_2$O | 750 ml (B W/V % fluid) |
| CaCl$_2$ | 75 ml (2 W/V % fluid) |
| CuSO$_4$.5H$_2$O | 112.5 ml (0.1 W/V % fluid) |
| Sodium L-glutamate | 30 g |
| Nicotinamide | 4.5 g |
| Casamino acid | 1800 g |
| Cysteine hydrochloride | 4.5 g |
| Tris-buffer | 12.5 l |

The above components were diluted with distilled water to make 150 l, adjusted to pH 7.0 to 7.2 and sterilized. Then, the following substances were added.

| Glutathione (reduced form) | 50 ml (1 W/V % fluid) |
|---|---|

-continued

| FeSO$_4$.7H$_2$O | 50 ml (1 W/V % fluid) |
|---|---|

TABLE 2

| Method of this invention | | | Detoxification with the addition of L-lysine | | | | | |
|---|---|---|---|---|---|---|---|---|
| LPF | HSF | Mouse protecting potency | LPF | HSF | Mouse protecting potency | LPF | HSF | Mouse protecting potency |
| o | o | 8.0 | x | x | 4.2$^\Delta$ | o | o | 3.0$^\Delta$ |
| o | o | 14.5 | x | x | 6.9 | o | o | 3.0$^\Delta$ |
| o | o | 12.8 | o | x | 11.3 | o | o | 7.0 |
| o | o | 10.0 | o | x | 10.0 | o | o | 5.0 |
| o | o | 12.0 | o | x | 10.2 | o | o | 2.2$^\Delta$ |
| o | o | 15.0 | o | x | 1.5$^\Delta$ | o | o | 8.4 |
| o | o | 13.0 | x | x | 8.0 | o | o | 2.0$^\Delta$ |
| o | o | 18.0 | x | o | 7.5 | o | o | 3.0$^\Delta$ |
| o | o | 11.0 | o | x | 14.1 | o | o | 1.8$^\Delta$ |
| o | o | 12.2 | | | | o | o | 4.5$^\Delta$ |
| o | o | 15.2 | | | | o | o | 4.5$^\Delta$ |
| o | o | 14.3 | | | | o | o | 8.0 |
| o | o | 18.1 | | | | o | o | 7.7 |
| o | o | 15.5 | | | | o | o | 5.9 |
| | | 13.5*[1] | | | 8.2*[1] | | | 4.7*[1] |

LPF
o: Not more than the equivalent of 0.5 LPU/ml
x: Other than o (Not acceptable)
HSF
o: Not more than the equivalent of 0.8 HSU/ml
x: Other than o (Not acceptable)
Mouse protecting potency: IU/ml
$\Delta$:Insufficient potency (Not acceptable)
*[1]: Mean value

EXAMPLE 2

The pertussis toxoid fluid obtained in Example 1, the diphtheria toxoid fluid meeting the Japanese Biological Products Standard and the tetanus toxoid meeting the same Standard were precipitation-treated as in Example 1 to prepare a precipitated-purified pertussis-diphtheria-tetanus trivalent vaccine. The composition of this vaccine was as follows:

| Pertussis toxoid | Proteineous N content; ca. 15 μg/ml |
|---|---|
| Diphtheria toxoid | ca. 30 Lf/ml |
| Tetanus toxoid | ca. 5 Lf/ml |
| Aluminum | ca. 0.2 mg/ml |
| Thimerosal | 0.01 W/V % |

The principal properties of this trivalent vaccine are as follows: Hydrogen ion concentration (reciprocal), 7.0; rabbit pyrogenicity (diluted 50-fold with saline and injected intravenously at 1 ml/kg body weight), negative; mouse body weight loss, not more than the equivalent of 10 BWDU (Body weight decrease units as determined by the method described in J. Med. Sci. Biol. 21, 115–135)/ml; mouse leukocytosis promoting activity, not more than the equivalent of 0.5 LPU/ml; mouse histamine sensitizing activity, not more than the equivalent of 0.8 HSU/ml; pertussis toxoid potency, the equivalent of 8 IU/ml; diphtheria toxoid potency, the equivalent of 45 IU/ml; tetanus toxoid potency, the equivalent of 30 IU/ml.

The trivalent vaccine can be administered to humans, for example, by the following schedule:

To infants of 3 to 48 month-age 0.5 ml each of the vaccine is inoculated subcutaneously 3 times with intervals of 2 to 8 weeks. Twelve to eighteen months after the last inoculation, further 0.5 ml of the vaccine is subcutaneously inoculated to each of the infants.

What is claimed is:

1. A method of producing a pertussis toxoid, which comprises removing endotoxin from a culture supernatant of a *Bordetella pertussis* phase I strain or a concentrate thereof, flocculating pertussis exotoxin in the resultant fluid by permitting formaldehyde to act upon the fluid in the substantial absence of basic amino acid and dispersing the flocculent mass in the resulting suspension of ultrasonication.

2. A method of claim 1, wherein the flocculation is performed by admixing formalin or a dilution thereof with the fluid in the substantial absence of basic amino acid and incubating the mixture.

3. A method of claim 2, wherein the incubation is continued until the pertussis exotoxin is substantially detoxified.

4. A method of claim 2, wherein formalin or a dilution thereof is admixed with the fluid, with no addition of basic amino acid, to give a concentration of about 0.1 to 0.6 v/v % in terms of formalin, and the mixture is incubated at about 32° to 42° C. for about 3 to 14 days.

5. A method of claim 1, wherein the removal of endotoxin is accomplished by contrifuging the culture supernatant or concentrate thereof on a sucrose density gradient of about 0 to 60 w/w % at R max. about 62,000 to 122,000 G for about 10 to 24 hours.

6. A method of claim 1, wherein a dialysis treatment is interposed between the respective steps.

7. A method of claim 1, wherein the culture supernatant is concentrated by salting out with use of ammonium sulfate, and endotoxin is removed from the resulting concentrate.

8. A method of claim 1, wherein *Bordetella pertussis* phase I strain is Tohama phase I strain.

* * * * *

UNITED STATES PATENT AND TRADEMARK OFFICE
CERTIFICATE OF CORRECTION

PATENT NO. : 4,455,297

DATED : June 19, 1984

INVENTOR(S) : Yukio Syukuda et al.

It is certified that error appears in the above-identified patent and that said Letters Patent is hereby corrected as shown below:

Column 7, line 8 (last line of claim 1), change "of" to --by--.

Signed and Sealed this

Twentieth Day of April, 1993

*Attest:*

MICHAEL K. KIRK

*Attesting Officer*      *Acting Commissioner of Patents and Trademarks*

UNITED STATES PATENT AND TRADEMARK OFFICE

CERTIFICATE EXTENDING PATENT TERM
UNDER 35 U.S.C. § 156

PATENT NO.:     4,455,297

DATED:          June 19, 1984

INVENTORS:      Yukio Syukuda et al.

PATENT OWNER:   Takeda Chemical Industries, Ltd.

This is to certify that there has been presented to the

COMMISSIONER OF PATENTS AND TRADEMARKS an application under 35 U.S.C. § 156 for an extension of the patent term. Since it appears that the requirements of the law have been met, this certificate extends the term of the patent for the period of 1,642 DAYS with all rights pertaining thereto as provided by 35 U.S.C. § 156(b).

I have caused the seal of the Patent and Trademark Office to be affixed this 20th day of May 1993.

Michael K. Kirk
Acting Commissioner of Patents and Trademarks